US00RE42645E

(19) United States
(12) Reissued Patent
Crum

(10) Patent Number: US RE42,645 E
(45) Date of Reissued Patent: Aug. 23, 2011

(54) NUTRITIONAL OR THERAPEUTIC COMPOSITIONS AND METHODS TO INCREASE BODILY GLUTATHIONE LEVELS

(76) Inventor: Albert Crum, Rhinebeck, NY (US)

( * ) Notice: This patent is subject to a terminal disclaimer.

(21) Appl. No.: 11/371,804

(22) Filed: Mar. 9, 2006

Related U.S. Patent Documents

Reissue of:
(64) Patent No.: 6,592,908
Issued: Jul. 15, 2003
Appl. No.: 10/252,957
Filed: Sep. 23, 2002

U.S. Applications:
(62) Division of application No. 11/181,001, filed on Jul. 13, 2005, now Pat. No. Re. 39,734.

(51) Int. Cl.

| | |
|---|---|
| ***A61K 31/095*** | (2006.01) |
| ***A61K 33/04*** | (2006.01) |
| ***A61K 31/197*** | (2006.01) |
| ***A61K 31/198*** | (2006.01) |
| ***A61P 3/02*** | (2006.01) |
| ***A61P 37/04*** | (2006.01) |

(52) U.S. Cl. ..... 424/702; 514/5.5; 514/21.9; 514/547; 514/556; 514/557; 514/558; 514/561; 514/562; 514/706; 514/824; 514/825; 514/836; 514/885; 514/905

(58) Field of Classification Search ..... 424/702; 514/556–558, 561, 562, 706, 824, 825, 836, 514/885, 905, 2, 547
See application file for complete search history.

(56) References Cited

U.S. PATENT DOCUMENTS

| | | | | |
|---|---|---|---|---|
| 5,550,146 | A | 8/1996 | Acosta et al. | |
| 5,576,351 | A * | 11/1996 | Yoshimura et al. | 514/565 |
| 5,719,133 | A | 2/1998 | Schmidl et al. | |
| 6,495,170 | B1 | 12/2002 | Smit et al. | |
| 2001/0048948 | A1 | 12/2001 | Crum et al. | |

FOREIGN PATENT DOCUMENTS

| | | |
|---|---|---|
| GB | 2 292 522 | 2/1996 |
| GB | 2292522 | * 2/1996 |
| RU | 2096034 | * 11/1997 |
| WO | 98/15614 | 4/1998 |

OTHER PUBLICATIONS

Basic Medical Biochemistry, Velker, J. (ed.), Williams & Wilkins, Baltimore, 1996, pp. 598-601.*
Martindale The Extra Pharmacopoeia, 30th ed., The Pharmaceutical Press, London, 1993, p. 1047.*
Considine, D.M. et al. Van Nostrand's Scientific Encyclopedia, 7th ed., Van Nostrand Reinhold, New York, pp. 128-129 (1989).*
Derwent abstract 1998-320409; abstracting RU 2096034 (1997).*
BIOSIS abstract 2001:509422 (2001).*
PubMed Abstract 61. Powell et al. "Restoration of Glutathione Levels in Vascular Smooth Muscle Cells Exposed to High Glucose Conditions." *Free Radic Biol Med.* (2001) Nov. 15; 31 (10):1149-1155.
PubMed Abstract 84. Bender et al. "Characterization of Cystine Uptake in Cultured Astrocytes." *Neurochem Int.* (2000) Aug.-Sep.; 37 (2-3):269-276.
PubMed Abstract 123. Wang et al. "Hepatic Export of Glutathione and Uptake of Constituent Amino Acids, Glutamate and Cysteine, in Broilers in Vivo." *Poult Sci.* (1998) Oct.; 77 (10):1556-1564.
PubMed Abstract 137. Tachi et al. "High Concentration of Glucose Causes Impairment of the Function of the Glutathione Redox Cycle in Human Vascular Smooth Muscle Cells." *FEBS Lett.* (1998) Jan. 2; 421 (1):19-22.
PubMed Abstract 139. Kranich et al. "Utilization of Cysteine and Cysteine Precursors for the Synthesis of Glutathione in Astroglial Cultures: Preference for Cystine." *Glia.* (1998) Jan.: 22 (1):11-18.
PubMed Abstract 141. Lu, SC. "Regulation of Hepatic Glutathione Synthesis." *Semin Liver Dis.* (1998) 18(4):331-343.
PubMed Abstract 143. Knickelbein et al. "Characterization of Multiple Cysteine and Cystine Transporters in Rat Alveolar Type II Cells." *Am J Physiol.* (1997) Dec.; 273(6 Pt 1):L1147-1155.
PubMed Abstract 150. Sayato et al. "Selenium Methylation and Toxicity Mechanism of Selenocystine." *Yakugaku Zasshi* (1997) Nov.; 117 (10-11):665-672.
PubMed Abstract 159. van Klaveren et al. "Cellular Glutathione Turnover in Vitro, with Emphasis on Type II Pneumocytes." *Eur Respir J.* (1997) Jun.; 10(6):1392-1400.
PubMed Abstract 160. Froissard et al. "Role of Glutathione Metabolism in the Glutamate-Induced Programmed Cell Death of Neuronal-Like PC12 Cells." *Eur J Pharmacol.* (1997) May 12;326 (1):93-99.
PubMed Abstract 167. Ochi, T. "Arsenic Compound-Induced Increases in Glutathione Levels in Cultured Chinese Hamster V79 Cells and Mechanisms Associated with Changes in Gamma-Glutamylcysteine Synthetase Activity, Cystine Uptake and Utilization of Cysteine." *Arch Toxicol.* (1997); 71(12):730-740.
PubMed Abstract 172. Kranich et al. "Different Preferences in the Utilization of Amino Acids for Glutathione Synthesis in Cultured Neurons and Astroglial Cells Derived from Rat Brain." *Neurosci Lett.* (1996) Nov. 29; 219 (3):211-214.
PubMed Abstract 173. Pan et al. "Increased Uptake of L-Cysteine and L-Cystine by Nerve Growth Factor in Rat Pheochromocytoma Cells." *Brian Res.* (1996) Nov. 18; 740 (1-2):21-26.
PubMed Abstract 177. Mills et al. "Differential Distribution of Free and Bound Glutathione and Cyst(e)ine in Human Blood." *Biochem Pharmacol.* (1996) Aug. 9; 52(3):401-406.
PubMed Abstract 186. Sagara et al. "Glutathione Efflux from Cultures Astrocytes." *J Neurochem.* (1996) May; 66 (5):1876-1881.
PubMed Abstract 187. Rathbun et al. "Prevention of Acetaminophen- and Naphthalene-Induced Cataract and Glutathione Loss by CySSME." *Invest Ophthalmol Vis Sci.* (1996) Apr.; 37 (5):923-929.
PubMed Abstract 193. Deneke et al. "Mechanisms of Use of Extracellular Glutathione by Lung Epithelial Cells and Pulmonary Artery Endothelial Cells." *Am J Respir Cell Mol Biol.* (1995) Jun.; 12 (6):662-668.
PubMed Abstract 195. O'Connor et al. "Biosynthesis and Maintenance of GSH in Primary Astrocyte Cultures: Role of L-Cystine and Ascorbate." *Brain Res.* (1995) May 22; 680 (1-2):157-163.

(Continued)

*Primary Examiner* — John Pak
(74) *Attorney, Agent, or Firm* — Blank Rome LLP

(57) ABSTRACT

Nutritional or therapeutic compositions containing glutamic acid, cystine, glycine and a selenium precursor and methods for their utilization to increase glutathione synthesis and thereby enhance the immune system are described.

17 Claims, No Drawings

OTHER PUBLICATIONS

PubMed Abstract 214. Cotgreave et al. "A Role for Gamma-Glutamyl Transpeptidase in the Transport of Cystine into Human Endothelial Cells: Relationship to Intracellular Glutathione." *Biochim Biophys Acta.* (1994) Jul. 21; 1222 (3):375-382.
PubMed Abstract 231. Sagara et al. "Maintenance of Neuronal Glutathione by Glial Cells." *J Neurochem.* (1993) Nov.; 61 (5):1672-1676.
PubMed Abstract 232. Sagara et al. "Cystine Uptake and Glutathione Level in Fetal Brain Cells in Primary Culture and in Suspension." *J Neurochem.* (1993) Nov.; 61 (5):1667-1671.
PubMed Abstract 255. Phelps et al. "Elevation of Glutathione Levels in Bovine Pulmonary Artery Endothelial Cells by N-Acetylcysteine." *Am J Respir Cell Mol Biol.* (1992) Sep.; 7 (3):293-299.
PubMed Abstract 265. Deneke et al. "Endothelial Cell Cystine Uptake and Glutathione Increase with N,N-bis(2-chloroethyl)-N-Nitrosourea Exposure." *Am J Physiol.* (1992) Mar.; 262 (3 Pt 1):L301-304.
PubMed Abstract 266. Brandi et al. "Differential Effect of the Amino Acid Cystine in Cultured Mammalian and Bacterial Cells Exposed to Oxidative Stress." *Mutat Res.* (1992) Mar.; 281 (3):157-161.
PubMed Abstract 271. Droge et al. "Modulation of Lymphocyte Functions and Immune Responses by Cysteine and Cysteine Derivatives." *Am J Med.* (1991) Sep. 30; 91 (3C):140S-144S.
PubMed Abstract 292. Atzori et al. "Growth-Associated Modifications of Low-Molecular-Weight Thiols and Protein Sulfhydryls in Human Bronchial Fibroblasts." *J Cell Physiol.* (1990) Apr.; 143 (1):165-171.
PubMed Abstract 298. Bannai et al. "Induction of Cystine Transport Activity in Human Fibroblasts by Oxygen." *J Biol Chem.* (1989) Nov. 5; 264 (31):18480-18484.
PubMed Abstract 309 Wagner, B. "Glutathione in Tetrahymena thermophila." *J Protozool* (1989) 36(1):92-5.
PubMed Abstract 314 Siegel, D.A., et al. "Effect of pairing in vitro on the glutathione level of male Schistosoma mansoni." J Parasitol (1988) 74(4):524-31.
PubMed Abstract 316 Nygaard, M.E., et al. "Sulfhydryl-related reduction of the mitotic inhibition and cell inactivation induced by pyrimidine analogs." Anticancer Drug Des. (1988) 3(1):15-24.
PubMed Abstract 320 Ishii, T., et al. "Regulation of glutathione levels in mouse spleen lymphocytes by transport of cysteine." J. Cell Physiol. (1987) 133(2):330-6.
PubMed Abstract 369 Mickelson, M.N., et al. "Cystine antagonism of the antibacterial action of lactoperoxidase-thiocyanate-hydrogen peroxide on *Streptococcus agalactiae*." Appl Environ Microbiol (1984) 47(2):338-42.
PubMed Abstract 372 Orrenius, S., et al. "Turnover and functions of glutathione studied with isolated hepatic and renal cells." Fed Proc (1983) 42(15):3177-88.
PubMed Abstract 379 Ohmori, H., et al. "Mechanism of augmentation of the antibody response in vitro by 2-mercaptoethanol in murine lymphocytes. II. A major role of the mixed disulfide between 2-mercaptoethanol and cysteine." Cell Immunol (1983) 79(1):173-85.
PubMed Abstract 391 Bannai, S., et al. "Adaptive enhancement of cystine and glutamate uptake in human diploid fibroblasts in culture." Biochim Biophys Acta (1982) 721(1):1-10.
PubMed Abstract 394 Bannai, S., et al. "Transport of cystine and cysteine and cell growth in cultured human diploid fibroblasts: effect of glutamate and homocysteate." J Cell Physiol (1982) 112(2):265-72.
PubMed Abstract 405 Moldeus, P., et al. "Turnover of cellular glutathione in isolated rat-kidney cells. Role of cystine and methionine." Eur J Biochem (1981) 116(1):13-6.
PubMed Abstract 406 Ishii, T., et al. "Mechanism of growth promotion of mouse lymphoma L1210 cells in vitro by feeder layer or 2-mercaptoethanol." J Cell Physiol (1981) 107(2):283-93.
PubMed Abstract 422 Rafter, G.W., et al. "Disulfide-disulfide interchange catalyzed by a liver supernatant enzyme." Biochim Biophys Acta (1979) 567(1):18-23.
PubMed Abstract 446 Thompson, G. A., et al. "Utilization of L-cystine by the gamma-glutamyl transpeptidase-gamma-glutamyl cyclotransferase pathway." Proc Nati Acad Sci U S A (1975) 72(6):1985-8.
PubMed Abstract 23 Alhamdan, A.A. "The effect of dietary supplementation of N-acetyl-L-cysteine on glutathione concentration and lipid peroxidation in cigarette smoke-exposed rats fed a low-protein diet." Saudi Med J. (2005) 26(2):208-14.
PubMed Abstract 38 Aliciguzel, Y., et al. "N-acetyl cysteine, L-cysteine, and beta-mercaptoethanol augment selenium-glutathione peroxidase activity in glucose-6-phosphate dehydrogenase-deficient human erythrocytes." Clin Exp Med (2004) 4(1):50-5.
PubMed Abstract 74 Yildiz, D. "Inhibition of tumor growth by replacing glutathione with N-acetyl-L-cysteine." Med Hypotheses (2004) 63(1):80-2.
PubMed Abstract 98 Wu, G., et al. "Glutathione metabolism and its implications for health." J Nutr. (2004) 134(3):489-92.
PubMed Abstract 440 Tuttle, S., et al. "Radiation-sensitive tyrosine phosphorylation of cellular proteins: sensitive to changes in GSH content induced by pretreatment with N-acetyl-L-cysteine or L-buthionine-S,R-sulfoximine." Int J Radiat Oncol Biol Phys. (1998) 42(4):833-8.
PubMed Abstract 549 Hou, Y., et al. "Seleno compounds and glutathione peroxidase catalyzed decomposition of S-nitrosothiols." Biochem Biophys Res Commun. (1996) 228(1):88-93.
PubMed Abstract 572 Holleschau, A.M., et al. "An HPLC radiotracer method for assessing the ability of L-cysteine prodrugs to maintain glutathione levels in the cultured rat lens." Curr Eye Res. (1996) 15(5):501-10.
PubMed Abstract 9 Hammarqvist, F., et al. "Free amino acid and glutathione concentrations in muscle during short-term starvation and refeeding." Clin Nutr. (2005) 24(2):236-43.
PubMed Abstract 10 Curi, R., et al. "Glutamine-dependent changes in gene expression and protein activity." Cell Biochem Funct. (2005) 23(2):77-84.
PubMed Abstract 15 Soh, H., et al. "Glutamine regulates amino acid transport and glutathione levels in a human neuroblastoma cell line." Pediatr Surg Int. (2005) 21(1):29-33.
PubMed Abstract 44 Evans, M.E., et al. "Glutamine prevents cytokine-induced apoptosis in human colonic epithelial cells." J Nutr. (2003) 133(10):3065-71.
PubMed Abstract 70 Valencia, E., et al. "Impact of oral L-glutamine on glutathione, glutamine, and glutamate blood levels in volunteers." Nutrition (2002) 18(5):367-70.
PubMed Abstract 124 Wernerman, J., et al. "Glutathione status in critically-ill patients: possibility of modulation by antioxidants." Proc Nutr Soc. (1999) 58(3):677-80.
PubMed Abstract 180 Denno, R., et al. "Glutamine-enriched total parenteral nutrition enhances plasma glutathione in the resting state." J Surg Res. (1996) 61(1):35-8.
Veber, D.G., e al. "Synthesis of alpha-methyl-DL-glutathione." J. Med. Chm. (1967) 10(5): 968-9.
Meier, T., et al. "Promotion of Cyst(e)ine Uptake" *Methods Enzymol.* (1995) vol. 252, pp. 103-112.
PubMed Abstract 238. Vina et al. "Maintenance of GSH Content in Primary Astrocyte Cultures Under Oxidative Stress Conditions." *Biochem Soc Trans.* (1993) May; 21 (2):84S.
Ralf Dringen, et al; Glutathione Contents as as Indicator . . . Cultures; Journal of Neurochemistry; vol. 67, No. 4; May 19, 1996; pp. 1375-1382.
Guoyao Wu, et al; Gutathione Metabolism . . . for Health; American Society for Nutritional Sciences; 2004; pp. 489-492.
Shiro Bannai; Exchange Of Cystine . . . Fibroblast; The Journal of Biological Chemistry; vol. 261; No. 5; Feb. 15, 1986; pp. 2256-2263.
Kenji Miura, et al; Cystine Uptake and . . . Oxidative Stress; The American Physiological Society; 1992; pp. C50-C58.
Hideyo Sato et al; Distribution of Cystine/Glutamate . . . Mouse Brain; The Journal of Neuroscience, Sep. 15, 2002; 22(18):8028-8033.
Shelly C. Lu, Current Topics in Cellular Regulation (2000) 36:95-116.
Thomas Meier, et al. Methods in Enzymology (1995) 252:103-112.

Shelly C. Lu, The FASEB Journal (1999) 13:1169-1183.
Dale, W.M., et al. A study of the irradiation of catalase by ionizing radiations in the presence of cysteine, crystine and glutathione. Biochem J (1950) 62(1):50-7.
Hutchin, M.E., et al. "Microbiological determination of cystine, systeine, and glutathione in plasma." J Biol Chem (1950) 185(2):839-43.
Schulman, J., et al, "Cystine, Cysteine, and Glutathione Metabolism in Normal and Cystinotic Fibroblasts in Vitro, and in Cultured Normal Amniotic Fluid Cells" Clin. Chim. Acta (1972) 37(53-58).
PubMed Abstract Phelps, DT., et al. Am J Respir Cell Mol Biol. 1992 Sep. 7(3):293-9.
PubMed Abstract of Deneke SM, et al . Am J Respir Cell Mol Biol. 1995 Jun.; 12(6);662-8.
Veber, D.F., et al. "Synthesis of alpha-methyl-DL-g-glutathione." J Med Chm (1967) 10(5):968-9.
Juan R. Vina, et al. "Maintenance of GSH Content in Primary Astrocyte Cultures Under Oxidative Stress Conditions" Biochemical Society Transactions (1993) 21:845.

* cited by examiner

NUTRITIONAL OR THERAPEUTIC COMPOSITIONS AND METHODS TO INCREASE BODILY GLUTATHIONE LEVELS

Matter enclosed in heavy brackets [ ] appears in the original patent but forms no part of this reissue specification; matter printed in italics indicates the additions made by reissue.

*More than one application for the Reissue of U.S. Pat. No. 6,592,908 has been filed. The reissue applications are the present application and U.S. Ser. No. 11/181,001, filed Jul. 13, 2005, and issued as U.S. Pat. RE 39,734 on Jul. 17, 2007.*

*STATEMENT OF PRIORITY*

*This application is a division of U.S. Ser. No. 11/181,001, filed Jul. 13, 2005 and which issued as U.S. Pat. RE 39,734 on Jul. 17, 2007, which is a reissue of U.S. Pat. No. 6,592,908 which issued on Jul. 13, 2005 from U.S. Ser. No. 10/252,957, filed Sep. 23, 2002, the disclosures of which are hereby incorporated by reference herein.*

FIELD OF THE INVENTION

This invention relates to nutritional or therapeutic compositions useful for treating mammals to increase their body content of glutathione above a pretreatment level thereby to enhance the immune activity of the treated mammal. More specifically, it relates to compositions containing a selenium compound together with a glutathione precursor which is a mixture of glutamic acid, cystine and glycine.

BACKGROUND OF THE INVENTION

Glutathione is a tripeptide and a major reducing agent in the mammalian body. Its chemical structure is:

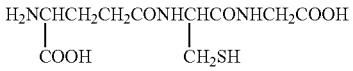

or, more simply

GLU-CYS-GLY

Its chemical name is glutamyl-cysteinyl-glycine.

Like many other small peptides in the mammalian body, it is not synthesized by procedures involving DNA, RNA and ribosomes. Rather, it is synthesized from the amino acids available in the body by procedures utilizing enzymes and other body components such as adenosine triphosphate as an energy source.

It is generally recognized that many disease processes are attributed to the presence of elevated levels of free radicals, reactive oxygen species (ROS) and reactive nitrogen species (RNS), such as superoxide, hydrogen peroxide, singlet oxygen, peroxynitrite, hydroxyl radicals, hypochlorous acid (and other hypohalous acids) and nitric oxide.

Mammalian cells have numerous mechanisms to eliminate these damaging free radicals and reactive species. One such mechanism includes the glutathione system, which plays a major role in direct destruction of reactive oxygen compounds and also plays a role in the body's defense against infection.

It is known that insufficient levels of glutathione may result in the onset of numerous diseases. Diseases of aging appear to be associated with a drop in glutathione levels. Moreover, since there is no evidence of transport of glutathione into cells, glutathione must be produced intra cellularly.

One of the most important contributions of glutathione to mammalian health is its participation in the proper functioning of the immune system to respond to infection or other types of trauma. It is known that weakening of the immune system caused by infection or other traumas occurs concurrently with depletion of glutathione in body tissues. It is known, also, that such weakening can be reversed by replenishing the supply of glutathione. It is believed that glutathione accomplishes its salutary effects by protecting immune cells against the ravages of oxidizing agents and free radicals.

There is a need for compositions and methods to aid in elimination of damaging free radicals and reactive oxygen and nitrogen species. One possible mechanism for achieving this may be through enhancement of glutathione levels in patients utilizing precursors for glutathione synthesis.

There is some question as to whether orally ingested glutathione is available to enhance the immune system. Since it is a tripeptide, conventional wisdom suggests that it would be hydrolyzed in the intestinal system to release the free amino acids. Even if some of the tripeptide gets through the gastrointestinal wall intact, it is questionable whether it can be absorbed as such into the individual cell, rather than being synthesized intracellularly. Some experts are of the opinion that glutathione resists hydrolysis when taken orally. In any event, it is generally acknowledged that an increase in tissue and cellular concentrations of glutathione facilitates resistance to infective agents by enhancing the immune system.

The mucous membrane is the membrane which lines those body passages which communicate directly or indirectly with the exterior. For purposes of this invention, the important parts of the mucous membrane are those portions which line the oral passage, the nose, the anus and the vagina since the compositions are intended for sublingual, buccal, nasal, anal and or vaginal delivery. Oral delivery by sublingual or buccal routes is much preferred because of its convenience. Such delivery may be, for example, in the form of pills, lozenges and tablets which may be retained in the mouth until dissolved. In rare instances, parenteral delivery may be utilized, but this is normally not necessary.

BRIEF SUMMARY OF THE INVENTION

The essential components of the compositions of this invention are:

1. A selenium precursor together with
2. Glutamic acid, cystine and glycine.

The separate components serve as precursors for the metabolic formation of glutathione after they have been transported across the mucous membrane.

The compositions may be used alone but, normally they will be employed in association with one or more non-toxic pharmaceutically acceptable carriers appropriate to the method of administration.

The compositions will be utilized to increase the formation of glutathione and thus to enhance the immune activity of a mammal in need of such treatment. The effect of the treatment is such that after the treatment, the mammal will be more resistant to microbial infection or other trauma adversely affecting immune activity than before such treatment.

Because of their ability to increase production of glutathione, the compositions are useful to treat a wide variety of diseases associated with the presence of excess free radical or reactive oxygen or nitrogen species. These include, for example, cancer, Alzheimer's disease, arteriosclerosis, rheumatoid arthritis and other autoimmune diseases, cachexia, coronary artery disease, chronic fatigue syndrome, AIDS and others as will be apparent to the skilled artisan.

DETAILED DESCRIPTION OF THE INVENTION

In accordance with the present invention, the compositions described and claimed herein will contain components suitable for the anabolic production of glutathione once they have been transported through the mucous membrane. As presently conceived, the precursors of glutathione are glutamic acid, cystine and glycine.

It will be appreciated by the skilled artisan that the proposed components are amphoteric and therefore may be employed as non-toxic metal salts or acid addition salts. Typically, the salts are alkalic or alkaline earth metal salts, preferably sodium, potassium or calcium salts. Suitable acid addition salts include salts of hydrochloric, phosphoric and citric acid.

The amino acids may also be employed in the form of certain of their derivatives including esters and anhydrides which before or after transport through the mucous membrane will be modified into the form in which they will be joined together to form glutathione.

All of this will be readily appreciated by those skilled in the art. Accordingly, when the terms glutamic acid, cystine, glycine are employed both in the specification and claims they will be understood to mean not only the products themselves, but also those derivatives which can be converted to a unit of the glutathione molecule.

The sulfur containing amino acid in the compositions of this invention is cystine. The sulfur containing amino acid moiety in glutathione is cysteine. The latter contains a sulfhydryl group. In the former molecule, two cysteine molecules are joined via a disulfide bond.

However, it is not possible to utilize cysteine in compositions for mammals because it is somewhat toxic. Accordingly, in the compositions of this invention, cystine is used. Upon reductive cleavage of the disulfide bridge, two molecules of cysteine are formed. Thus each molecule of cystine is capable of forming two molecules, of cysteine, each of which will join with glutamic acid and glycine to form two molecules of glutathione.

Of course all amino acids employed in this invention, except glycine which does not form optical isomers, are in the natural or L-form.

Although wide variations are possible, it will be apparent that the optimum ratio of glutamic acid to cystine to glycine in the novel compositions described herein is 1:0.5: 1. If an excess of any acid is used, it will presumably be of nutritional value or may simply be metabolized.

As will be apparent to the skilled artisan, the only component in the novel compositions of this invention which may be toxic is selenium. Accordingly, in providing dosage units for mammalian administration by any selected route, the limiting factor is to avoid treatment either with single or multiple dosage units at such levels that the total delivery of selenium is close to its toxic limit.

The recommended daily allowances for elemental selenium as reported in The Pharmacological Basis of Therapeutics, Ninth Edition, page 1540, The McGraw-Hill Companies, 1996 are as follows:

| | Years | ug |
|---|---|---|
| Infants | 0.0-0.5 | 10 |
| | 0.5-1.0 | 15 |
| Children | 1-3 | 20 |
| | 4-6 | 20 |
| | 7-10 | 30 |
| Males | 11-14 | 40 |
| | 15-18 | 50 |
| | 19-24 | 70 |
| | 25-50 | 70 |
| | 51+ | 70 |
| Females | 11-14 | 45 |
| | 15-18 | 50 |
| | 19-24 | 55 |
| | 25-50 | 55 |
| | 50+ | 55 |
| Pregnant | — | 65 |
| Lactating | $1^{st}$ six months | 75 |
| | $2^{nd}$ six months | 75 |

The recommended daily dosage for humans therefore ranges from 10 to 75 μg per day. For animals the range may be generally higher but will, of course, depend upon the animal and its size.

The precise amount of the therapeutically useful compositions of this invention for daily delivery and the duration of the period of such delivery will depend upon the professional judgment of the physician or veterinarian in attendance. Numerous factors will be involved in that judgment such as age, body weight, physical condition of the patient or animal and the ailment or disorder being treated.

Selenium is one of numerous trace metals found in many foods. In the compositions of this invention, selenium may be employed as one of several non-toxic, water soluble organic or inorganic selenium compounds capable of being absorbed through the mucosal membrane. The presently preferred inorganic selenium compounds are aliphatic metal salts containing selenium in the form of selenite or selenate anions. However, organic selenium compounds are more preferred because they are normally less toxic than inorganic compounds. Other selenium compounds which may be mentioned by way of example include selenium cystine, selenium methionine, mono- and di-seleno carboxylic acids with about seven to eleven carbon atoms in the chain. Seleno Amino acid chelates are also useful. Any of these selenium compounds may be considered for use in the present invention as selenium precursors.

It is important for the practice of this invention that the selenium as employed in the composition be capable of transport through the mucosal membrane of the patient under treatment. For this reason, water insoluble selenium compounds are not generally useful.

For convenience, the term "selenium" is sometimes used hereinafter to include any of the various water soluble selenium products which can be transported through the mucosal membrane in the practice of this invention. It will be understood, however, that the particular forms of selenium compounds set forth herein are not to be considered limitative. Other selenium compounds, which exhibit the desired activity and are compatible with the other components in the mixture and are non-toxic, can be used in the practice of the invention. Many of them are available commercially.

In fact, the amount of selenium precursor employed in the novel compositions is only enough to provide a catalytic quantity of the element to activate the glutathione system. The catalytic quantity of selenium precursor utilized in the compositions of this invention is such that it will produce either in one dosage unit or in multiple dosage units sufficient elemental selenium to promote the production and activation of glutathione. Typically, this will be at or near the recommended daily allowance of selenium for the individual mammal under treatment. This amount will be well below the toxicity limit for elemental selenium. By way of non-limiting examples, a representative range of catalytic quantities of selenium precursors is set forth in the present application in paragraph [0026] on page 6, as shown to be effective based on the age of the individual.

As indicated above, the presently preferred method of transdermal delivery for the novel compositions is oral, either sublingual or buccal. It is convenient to provide dosage units for such delivery in the form of pills, lozenges or tablets such as gelled tablets which will slowly dissolve in the mouth.

Nasal delivery will typically be accomplished by sprays or drops. Suppositories will be useful for rectal or vaginal delivery.

This invention provides pharmaceutical compositions used in the method of the invention. Such compositions comprise a therapeutically effective amount of combined glutamic acid, cystine, glycine and a selenium precursor in a pharmaceutically acceptable carrier. In a particular embodiment, the term "pharmaceutically acceptable" means one that is generally recognized as safe, approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the active compounds are administered.

The compositions which may be provided in bulk or dosage unit form are prepared in accordance with standard pharmaceutical practice and may contain excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Sterile liquids, such as water and oils, including those of petroleum, animal, vegetable or synthetic origin, such as peanut oil, soybean oil, mineral oil, and sesame oil may also be useful. The composition, if desired, can also contain minor amounts of wetting or emulsifying agents, coloring agents or buffering agents.

Buffering agents are sometimes used in the compositions of the invention to maintain a relatively constant hydrogen ion concentration in the mouth (pH about 7.5) or other point of entry. An appropriate buffering agent may be selected from numerous known reagents including, for example phosphate, carbonate and bicarbonate systems. Alpha-lactalbumin is useful because of its buffering properties. Additionally, it is non-toxic, water soluble and contains appreciable amounts of the required amino acids.

The compositions may also contain mucous membrane penetration enhancers such as sodium lauryl sulphate, sodium dodecyl sulphate, cationic surfactants such as palmitoyl DL camitine chloride, cetylpyridinium chloride, nonionic surfactants such as polysorbate 80, polyoxyethylene 9-lauryl either, glyceryl monolaurate, polyoxyalkylenes, polyoxyethylene 20 cetyl ether, lipids such as oleic acid, bile salts such as sodium glycocholate, sodium taurocholate and related compounds.

Examples of these suitable carriers are described in Remington's Pharmaceutical Sciences, Nineteenth Edition (1990), Mack Publishing Company, Easton, Pa. in Handbook of Pharmaceutical Excipients, published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980). Compositions and methods of manufacturing compositions capable of absorption through the mucosal tissues are taught in U.S. Pat. No. 5,288,497. These publications are incorporated by reference herein in their entirety. They can be readily employed by the skilled artisan to devise methods of delivery other than those specifically described in this disclosure.

The compositions of the invention are most conveniently utilized in dosage units for oral administration. They may be used alone but are preferably provided as tablets, suitably sublingual tablets. Such tablets may be prepared in one a day form or for intermittent use throughout the day, for example every three hours.

The tablets will typically weigh from about 0.5 to 5 grams and will contain a therapeutically effective amount of the essential ingredients together with the selected vehicle. "Therapeutically effective" as used herein means the amount of the composition which is sufficient to achieve the desired result, i.e., enhancement of the immune system. It means that the immune system is more effective in combating infection after treatment than it was before treatment.

A particular advantage of the compositions of the invention is that they can be provided in a number of different forms and at dosage levels appropriate to the individual mammal being treated. For example, tablets, elixers, solutions, emulsions, powders, capsules and other forms can be provided for one a day treatment or successive treatments on the same day for animals or humans whether male or female, whether infant, adolescent or adult. The defining feature of this advantage is the amount of selenium precursor utilized since the other components are essentially non-toxic.

Referring to the table above, tablets and other forms of the immunoenhancing compositions can be prepared to provide any quantity of elemental selenium from less than 1 μg to 7.5 μg. For example, a tablet containing 10 μg of selenium methionine is capable of delivering 4 μg of elemental selenium, and 7.5 μg of selenium methionine is capable of delivering 3 μg of selenium. Tablets may be given several times per day to achieve the desired immune enhancing effect.

A one a day tablet weighing two grams may contain 200 mg or more of the composition. A similar tablet intended to be used every four hours may contain 50 mg to 100 mg or more of the therapeutically effective composition. Equivalent amounts of carrier and active components will be utilized in other compositions designed for other methods of administration.

The following examples are given by way of illustration only and are not to be considered a limitation since many apparent variations are possible without departing from the spirit or scope of the invention.

EXAMPLE 1 (TABLET)

| Ingredients: | |
|---|---|
| 89 mg | cystine |
| 75 mg | glycine |
| 147 mg | glutamic acid |
| 22.5 μg | polyvinylpyrolidone |
| 61.25 mg | lactose |
| 4.5 ml | alcohol SD3A-200 proof |
| 9 mg | stearic acid |
| 42.3 mg | corn starch |
| 10 μg | selenium methionine |

Blend the cystine, glycine, glutamic acid, polyvinylpyrrolidone and lactose together and pass through a 40 mesh screen. Add the alcohol slowly and knead well. Screen the wet mesh through a 4 mesh screen. Dry the granulation at 50 degrees centigrade for 10 hours. Pass the mixture of stearic acid, corn starch and selenium compound through a 60 mesh screen and tumble with the granulation until all the ingredients are well mixed. Compress using a 7/16 inch standard concave punch.

EXAMPLE 2 (TABLET)

| Ingredients: | |
|---|---|
| 178 mg | cystine |
| 150 mg | glycine |
| 294 mg | glutamic acid |
| 5 μg | selenium methionine |
| 126 mg | lactose |
| 78 mg | potato starch |
| 96 mg | ethyl cellulose |
| 54 mg | stearic acid |

Thoroughly mix the ingredients in a blender, dry, put through a 12 mesh screen and compress into tablet using a 13/32 inch concave punch.

What is claimed is:

[1. A nutritional or therapeutic composition useful for treatment of mammals to enhance immune activity comprising as the essential active ingredients a catalytic quantity of a selenium source together with a glutathione precursor which is a mixture of glutamic acid, cystine and glycine in a molar ratio of about 1:0.5:1, the amount of glutathione precursor being effective to increase the content of glutathione in the body tissue of the mammal above that of a pretreatment level thereby to enhance immune activity.]

[2. A composition of claim 1 in dosage unit form.]

[3. A composition of claim 1 in bulk form.]

[4. A composition of claim 2, wherein the dosage unit is for oral administration.]

[5. A composition of claim 2, wherein the dosage unit is for nasal administration.]

[6. A composition of claim 4, wherein the dosage unit is for sublingual administration.]

[7. A composition of claim 4, wherein the dosage unit is for buccal administration.]

[8. A composition of claim 1, useful for treating a human.]

[9. A composition of claim 1 useful for treating an animal.]

[10. A method of treating a mammal to increase the tissue glutathione concentration in said mammal which comprises treating a mammal in need of such treatment with a therapeutically effective amount of a composition comprising as the essential active ingredients a catalytic quantity of a selenium source together with a glutathione precursor which is a mixture of glutamic acid, cystine and glycine in a molar ratio of about 1:0.5:1.]

[11. A method of claim 10, wherein the mammal is an animal.]

[12. A method of claim 10, wherein the mammal is a human.]

*13. A composition for increasing the level of glutathione in a mammal consisting of:*

*(A) an anabolic precursor of glutathione, consisting of glutamic acid or a salt, an ester, or an anhydride thereof, cystine or a salt, an ester, or an anhydride thereof and glycine or a salt, an ester, or an anhydride thereof, which collectively convert to glutathione; and*

*(B) a source of selenium, in an amount that is non-toxic to the mammal on a daily total unit dosage delivery basis; wherein said source of selenium is selenium methionine, selenium cystine, a mono-seleno carboxylic acid with seven to eleven carbon atoms in a chain, or a di-seleno carboxylic acid with seven to eleven carbon atoms in a chain.*

*14. The composition according to claim 13 in unit dosage form.*

*15. The composition according to claim 13 in bulk form.*

*16. The composition according to claim 14 wherein the dosage unit is for oral administration.*

*17. The composition according to claim 14 wherein the dosage unit is for nasal administration.*

*18. The composition according to claim 14 wherein the dosage unit is for sublingual administration.*

*19. The composition according to claim 14 wherein the dosage unit is for buccal administration.*

*20. The composition according to claim 14 wherein the dosage unit is for anal or vaginal administration.*

*21. The composition of claim 13 wherein the mammal is a human.*

*22. The composition of claim 13 wherein one or more of said glutamic acid, cystine, and glycine are in the form of a salt, an ester, or an anhydride thereof.*

*23. The composition of claim 13 wherein the glutamic acid is in the form of a salt, an ester, or an anhydride thereof.*

*24. The composition of claim 13 wherein the cystine is in the form of a salt, an ester, or an anhydride thereof.*

*25. The composition of claim 13 wherein the glycine is in the form of a salt, an ester or an anhydride thereof.*

*26. The composition according to claim 13, wherein the source of selenium is in a mucosal-membrane transportable form.*

*27. A method of increasing the level of glutathione in a mammal comprising administering to said mammal an effective amount of a composition consisting of:*

*(A) an anabolic precursor of glutathione, consisting of glutamic acid or a salt, an ester, or an anhydride thereof, cystine or a salt, an ester, or an anhydride thereof and glycine or a salt, an ester or an anhydride thereof, which collectively convert to glutathione; and*

*(B) a source of selenium, in an amount that is non-toxic to the mammal on a daily total unit dosage delivery basis; wherein said source of selenium is selenium methionine, selenium cystine, a mono-seleno carboxylic acid with seven to eleven carbon atoms in a chain, or a di-seleno carboxylic acid with seven to eleven carbon atoms in a chain.*

*28. The method of claim 27 wherein cystine converts to cysteine in the intracellular formation of glutathione.*

*29. The method of claim 27 wherein the source of selenium provides a unit dosage on an elemental basis of from 1 μg to 7.5 μg of selenium.*

* * * * *